United States Patent
Cho et al.

(10) Patent No.: US 9,018,008 B2
(45) Date of Patent: Apr. 28, 2015

(54) THREE-DIMENSIONAL SCAFFOLD AND METHOD OF MANUFACTURING THE SAME

(75) Inventors: Dong-Woo Cho, Seoul (KR); Jong Young Kim, Daegu (KR); Jin-Hyung Shim, Pohang (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/511,188

(22) PCT Filed: Mar. 4, 2011

(86) PCT No.: PCT/KR2011/001516
§ 371 (c)(1),
(2), (4) Date: May 22, 2012

(87) PCT Pub. No.: WO2011/115381
PCT Pub. Date: Sep. 22, 2011

(65) Prior Publication Data
US 2012/0329156 A1 Dec. 27, 2012

(30) Foreign Application Priority Data
Mar. 19, 2010 (KR) ........................ 10-2010-0024736

(51) Int. Cl.
*C12N 5/00* (2006.01)
*A61K 9/14* (2006.01)
*A61L 27/14* (2006.01)
*A61L 27/52* (2006.01)
*A61L 27/56* (2006.01)
*C12M 1/12* (2006.01)

(52) U.S. Cl.
CPC ................. *A61L 27/14* (2013.01); *A61L 27/52* (2013.01); *A61L 27/56* (2013.01); *C12M 25/14* (2013.01); *C12N 5/0068* (2013.01); *C12N 2533/40* (2013.01); *C12N 2533/54* (2013.01); *C12N 2533/80* (2013.01)

(58) Field of Classification Search
USPC ........................................................ 435/397
See application file for complete search history.

(56) References Cited

U.S. PATENT DOCUMENTS

| | | | |
|---|---|---|---|
| 8,071,007 B1 * | 12/2011 | Teoh et al. ................ | 264/308 |
| 2003/0021823 A1 | 1/2003 | Landers et al. | |
| 2004/0126405 A1 * | 7/2004 | Sahatjian et al. ............ | 424/423 |
| 2006/0195179 A1 | 8/2006 | Sun et al. | |
| 2008/0020049 A1 | 1/2008 | Darling et al. | |
| 2008/0145639 A1 | 6/2008 | Sun et al. | |
| 2008/0193536 A1 * | 8/2008 | Khademhosseini et al. .. | 424/486 |
| 2008/0220042 A1 * | 9/2008 | Hashi et al. ................. | 424/423 |
| 2012/0089238 A1 * | 4/2012 | Kang et al. ................ | 623/23.72 |

FOREIGN PATENT DOCUMENTS

| | | | |
|---|---|---|---|
| CN | 101279850 | 10/2008 | |
| EP | 1053758 | 11/2000 | |
| KR | 10-2003-0032420 | 4/2003 | |
| KR | 10-2011-0025327 | 3/2011 | |
| KR | 10-2011-0077244 | 7/2011 | |
| WO | 03/004254 | 1/2003 | |
| WO | 2005/061018 | 7/2005 | |
| WO | 2006/091921 | 8/2006 | |
| WO | 2006/096791 | 9/2006 | |
| WO | WO 2008003320 A2 * | 1/2008 | ............. A61L 27/34 |
| WO | 2008/115160 | 9/2008 | |

OTHER PUBLICATIONS

Hutmacher, Scaffolds in tissue engineering bone and cartilage, Biomaterials 21 (2000), 2529-2543.*
Woodfield, Design of porous scaffolds for cartilage tissue engineering using a 3D fiber deposition technique, Biomaterials 25 (2004) 4149-4161.*
Nakamura et al., Biomatrices and biomaterials for future developments of bioprinting and biofabrication, Biofabrication, vol. 2, Mar. 10, 2010.*
Woodfield et al., Design of porous scaffolds for cartilage tissue engineering using a 3-D fiber-deposition technique, Biomaterials, 25, 4149-4161, 2004.*
State Intellectual Property Office of the P.R.C. Search Report dated Oct. 9, 2013, which was attached to the Office Action dated Oct. 17, 2013 of the corresponding application (Chinese Patent Application No. 201180011573.9).
Joon Young Kim, et al., "Cell adhesion and proliferation evaluation of SFF-based biodegradable scaffolds fabricated using a multi-head deposition system", Biofabrication, vol. 1, 015002, Republic of Korea (Mar. 2009).
European Patent Office, the extended European Search Report dated Dec. 12, 2014, of the corresponding European Patent Application No. 11756512.7.

* cited by examiner

*Primary Examiner* — Taeyoon Kim
*Assistant Examiner* — Srikanth Patury
(74) *Attorney, Agent, or Firm* — Lexyoume IP Meister, PLLC

(57) ABSTRACT

A scaffold having a reinforced tissue regeneration ability and a method of manufacturing the same are provided. The scaffold is formed in a lattice form by alternately stacking biodegradable synthetic polymer-hydrogel layers. In this case, the biodegradable synthetic polymer-hydrogel layer is formed by disposing a plurality of biodegradable synthetic polymer-hydrogel units including a biodegradable synthetic polymer and a hydrogel at a predetermined gap.

7 Claims, 9 Drawing Sheets

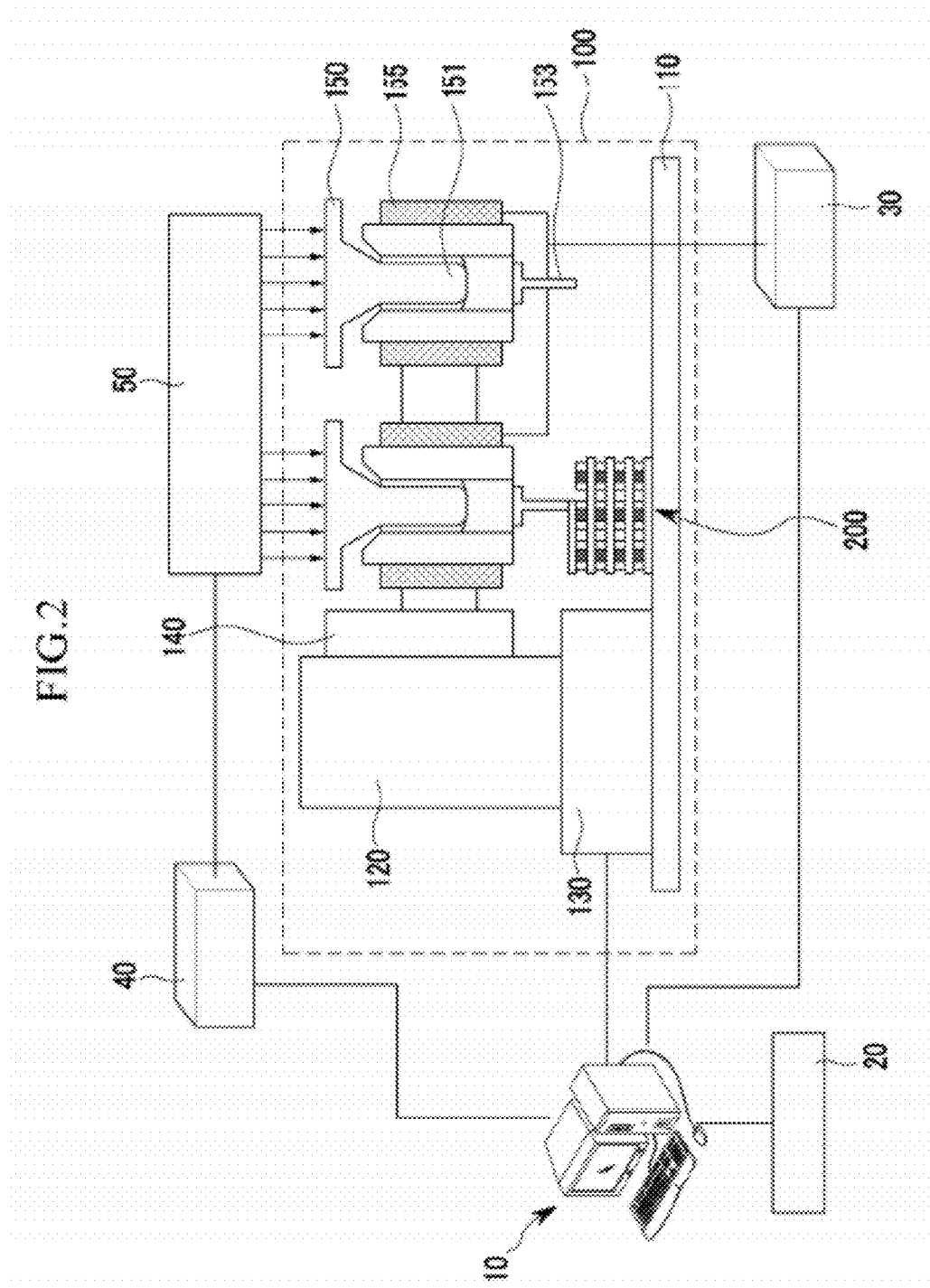

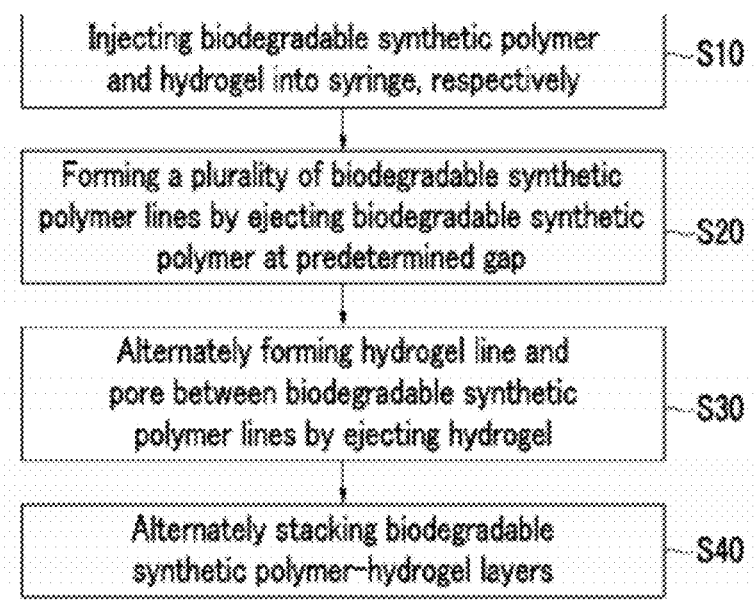

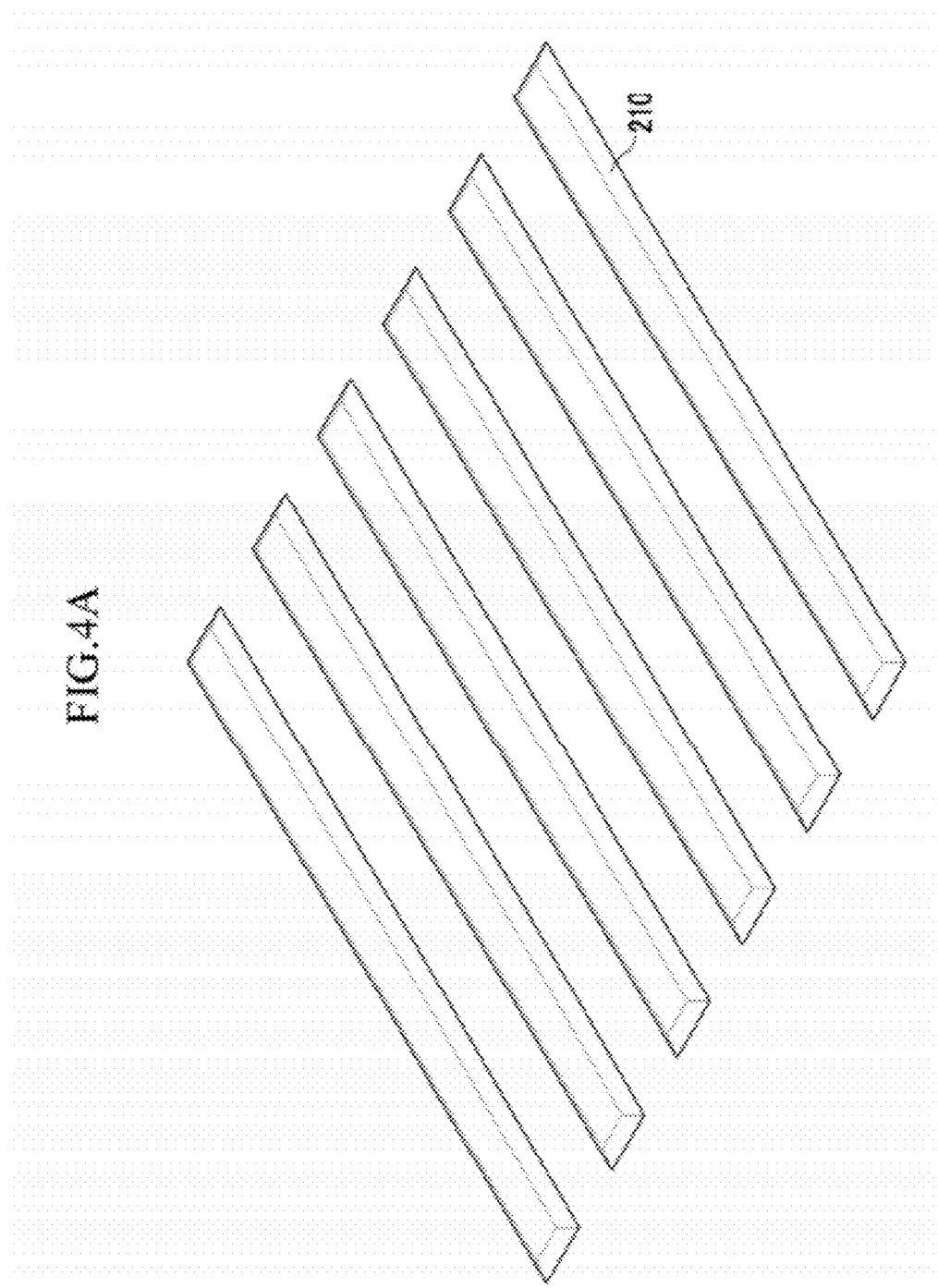

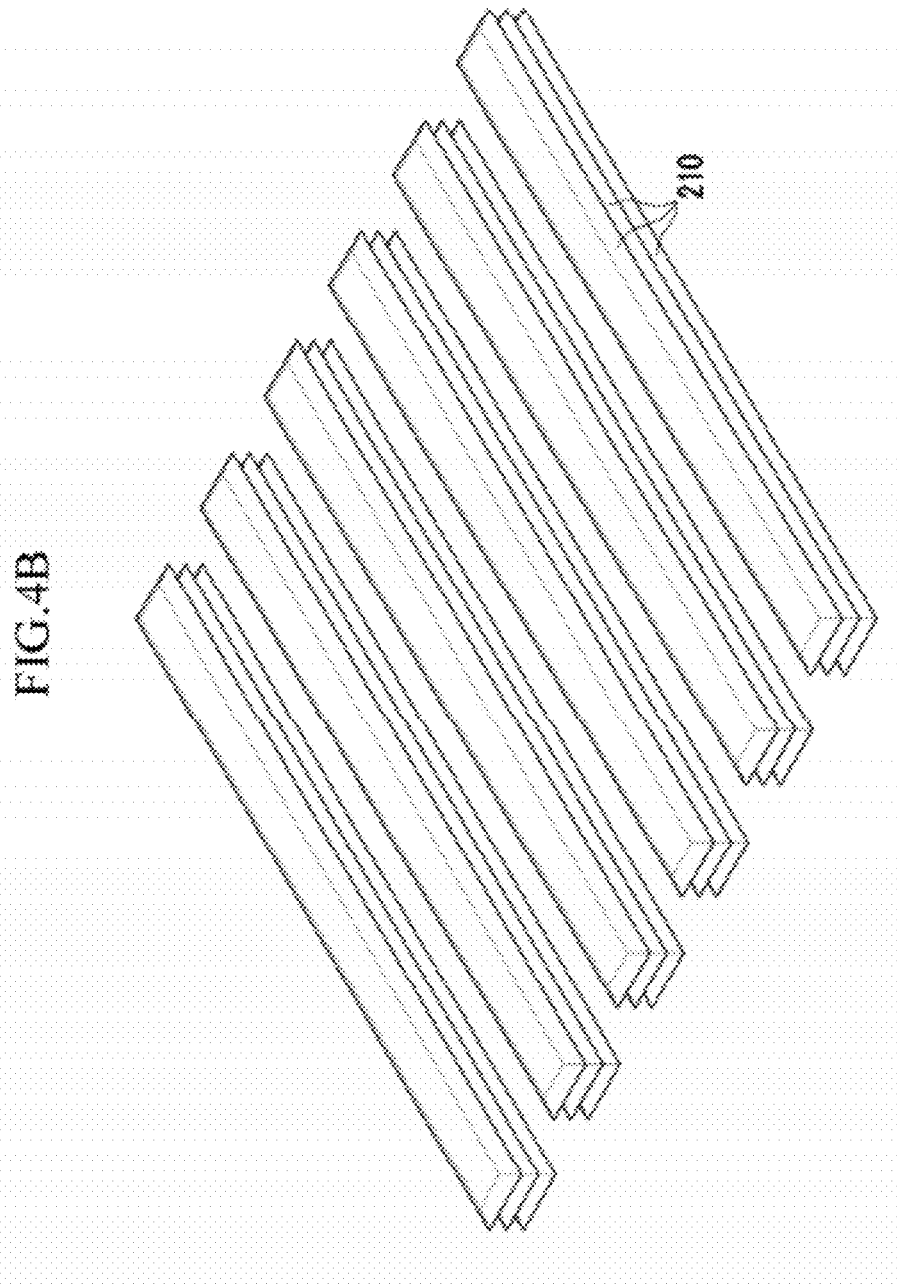

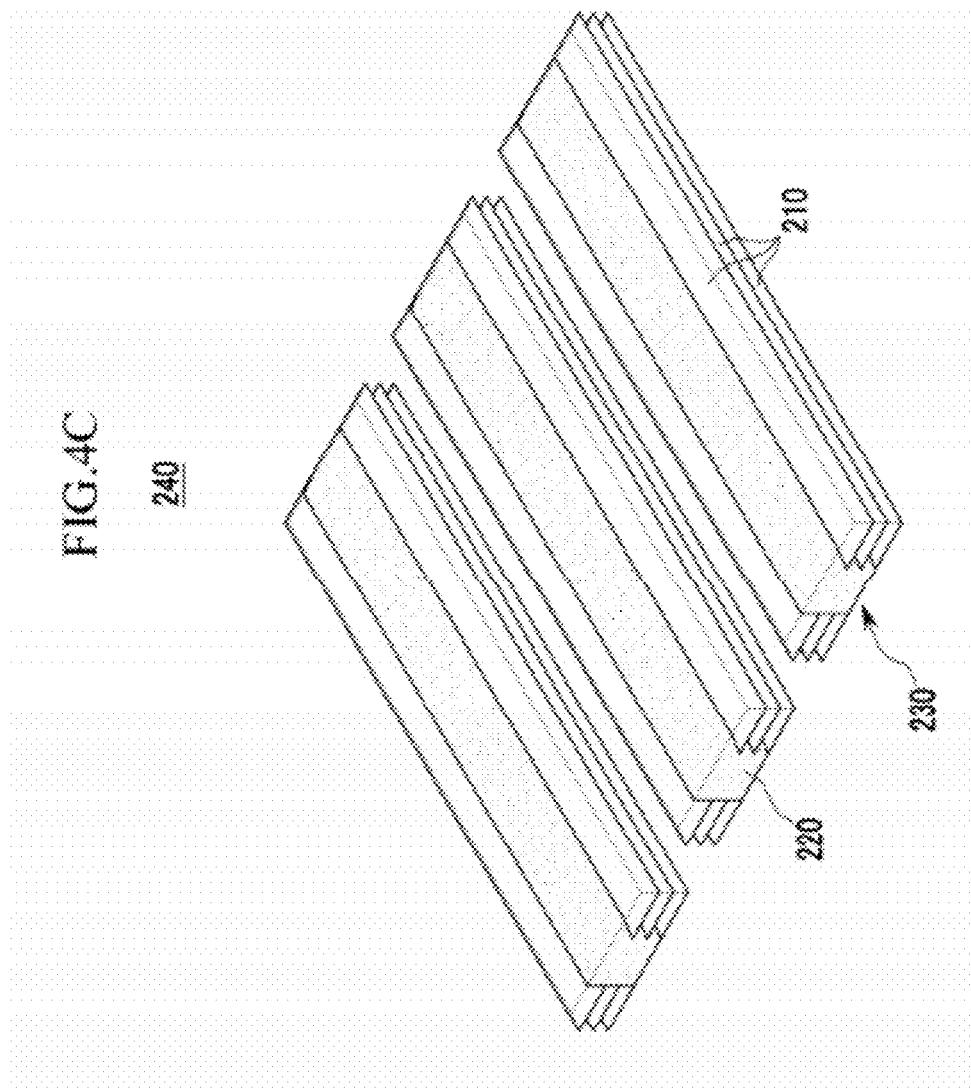

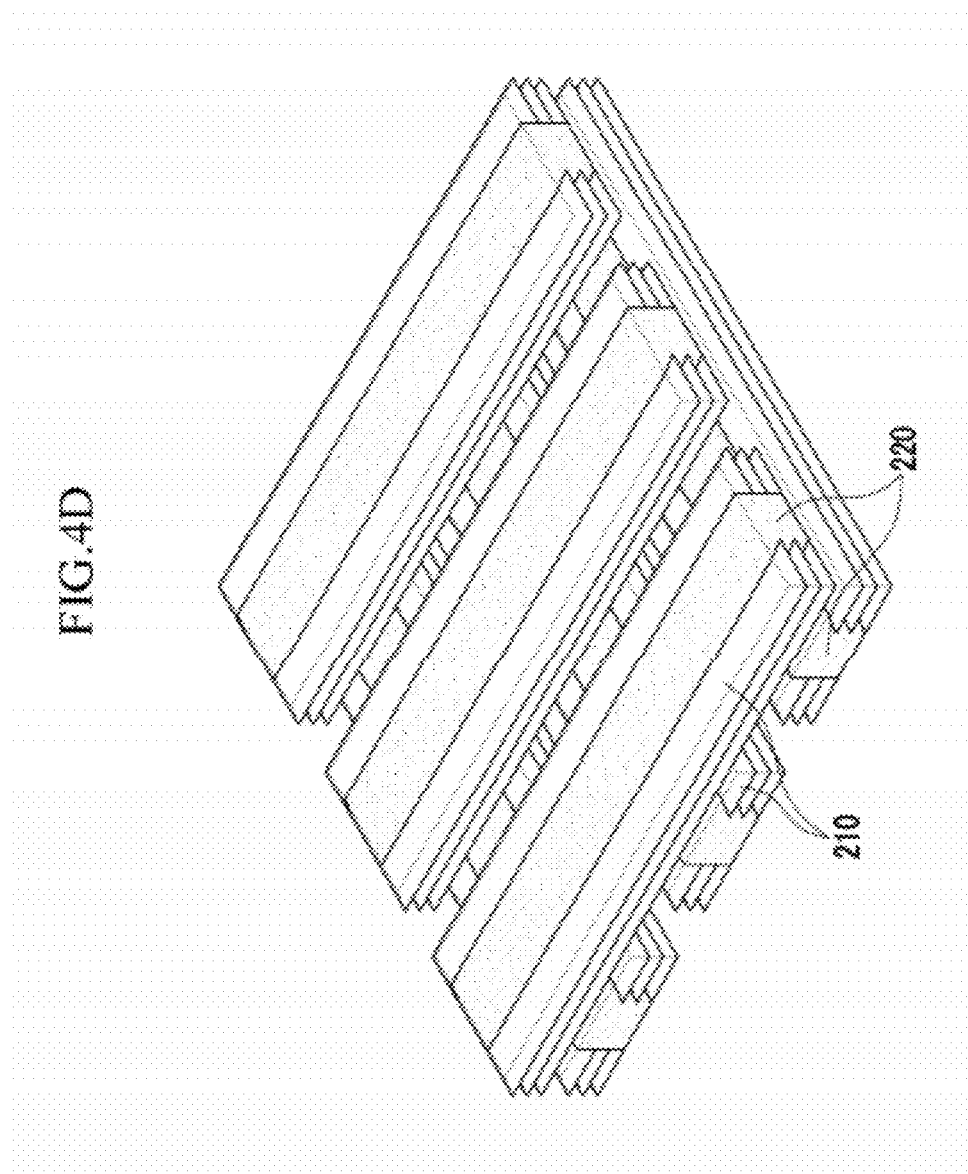

THREE-DIMENSIONAL SCAFFOLD AND METHOD OF MANUFACTURING THE SAME

CROSS-REFERENCE TO RELATED APPLICATION

This application claims priority to and the benefit of Korean Patent Application No. 10-2010-0024736 filed in the Korean Intellectual Property Office on Mar. 19, 2010, the entire contents of which are incorporated herein by reference.

BACKGROUND OF THE INVENTION (a) Field of the Invention

The present invention relates to a three-dimensional scaffold and a method of manufacturing the same. More particularly, the present invention relates to a three-dimensional scaffold that is formed with a biodegradable polymer and a hydrogel and a method of manufacturing the same.

(b) Description of the Related Art

A tissue engineering field is a technology field that cultivates a small quantity of extracted cell from a patient's tissue into a large quantity at the outside of the patient's body and that differentiates the cell to a three-dimensional tissue and that regenerates the three-dimensional tissue into a tissue and an organ in order to regenerate damaged internal organs and with respect to a tissue engineering field, in order to restore a function of various tissues and organs of a damaged human body, a research of various approach methods has been performed.

In tissue engineering, for three-dimensional cultivation of a tissue, a scaffold in which a cell can recognize as a three-dimensional environment is necessary, and in order to induce smooth deposition, propagation, and differentiation of a cell, the scaffold should have an appropriate extra cellular matrix (ECM) structure. Further, a scaffold should have a porous three-dimensional structure that is connected to an appropriate size for vein infiltration for movement of a cell, promotion of metabolism, and supply of nutritive elements and should sustain appropriate strength that can sustain the form for a tissue regeneration period.

Conventionally, in order to obtain such a three-dimensional scaffold, a method such as a gas foaming/salt leaching method, a phase separation method, a solvent-casting particulate-leaching method, and an emulsion freeze-drying method is used, and a scaffold that is manufactured by this method has a limitation in adjustment of a size, a position and a porosity of a pore of a porous structure. Further, in order to enhance a connection between pores within a scaffold, a porosity is much increased and thus a problem that mechanical strength is also lowered occurs.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a scaffold and a method of manufacturing the same having advantages of a reinforced tissue regeneration ability by fusing a biodegradable polymer and a hydrogel.

An exemplary embodiment of the present invention provides a scaffold that is formed in a lattice form by alternately stacking biodegradable synthetic polymer-hydrogel layers, wherein the biodegradable synthetic polymer-hydrogel layer is formed by disposing a plurality of biodegradable synthetic polymer-hydrogel units including a biodegradable synthetic polymer and a hydrogel at a predetermined gap.

The biodegradable synthetic polymer-hydrogel unit may be formed by interposing a hydrogel line between a pair of opposite biodegradable synthetic polymer lines.

The biodegradable synthetic polymer may include at least one of poly-lactic acid (PLA), poly-glycolic acid (PGA), polycaprolactone, and poly-lactic-co-glycolic acid (PLGA).

The hydrogel may be water-soluble and be one of collagen, gelatin, chitosan, alginic acid, and hyaluronic acid.

A growth factor that can adjust growth and a function of a cell may exist within the hydrogel, and the growth factor existing within the hydrogel may be one of a transforming growth factor-β (TGF-β), bone morphogenetic protein (BMP), a vein endothelial cell growth factor (VEGF) and an epithelial cell growth factor (EGF). A cell to regenerate may exist within the hydrogel.

Another embodiment of the present invention provides a method of manufacturing a scaffold, the method including: injecting a biodegradable synthetic polymer and a hydrogel into a first syringe and a second syringe, respectively; first ejecting of forming a plurality of biodegradable synthetic polymer lines at a predetermined gap by ejecting the biodegradable synthetic polymer that is injected into the first syringe; second ejecting of forming a biodegradable synthetic polymer-hydrogel layer by alternately forming hydrogel lines and pores between a plurality of biodegradable synthetic polymer lines by ejecting the hydrogel that is injected into the second syringe; and alternately stacking the biodegradable synthetic polymer-hydrogel layer by repeating the first ejecting and the second ejecting.

Further, after step of injection a biodegradable synthetic polymer, the method may further include controlling a temperature of the biodegradable synthetic polymer and the hydrogel through the temperature controller that is connected to the first and second syringes.

The biodegradable synthetic polymer may include at least one of PLA, PGA, polycaprolactone, and PLGA.

The hydrogel may be water-soluble and be one of collagen, gelatin, chitosan, alginic acid, and hyaluronic acid.

A growth factor that can adjust growth and a function of a cell may exist within the hydrogel, and the growth factor existing within the hydrogel is one of a TGF-β, BMP, a VEGF, and an EGF. A cell to regenerate may exist within the hydrogel.

According to an exemplary embodiment of the present invention, a cell deposition ability and a proliferation ability of a deposited cell can be improved, mechanical strength of a scaffold can be improved, and a size of a shape and a pore of the scaffold can be adjusted.

Further, a process speed can be improved using an automation system of a multi-head deposition system.

BRIEF DESCRIPTION OF THE DRAWINGS

FIG. 2 is a diagram illustrating a configuration of a multi-head deposition system for manufacturing a scaffold according to an exemplary embodiment of the present invention.

FIG. 3 is a flowchart illustrating a process of manufacturing a scaffold according to an exemplary embodiment of the present invention.

FIGS. 4A to 4E are perspective views sequentially illustrating a process of manufacturing a scaffold according to an exemplary embodiment of the present invention.

DETAILED DESCRIPTION OF THE EMBODIMENTS

Figure 1:
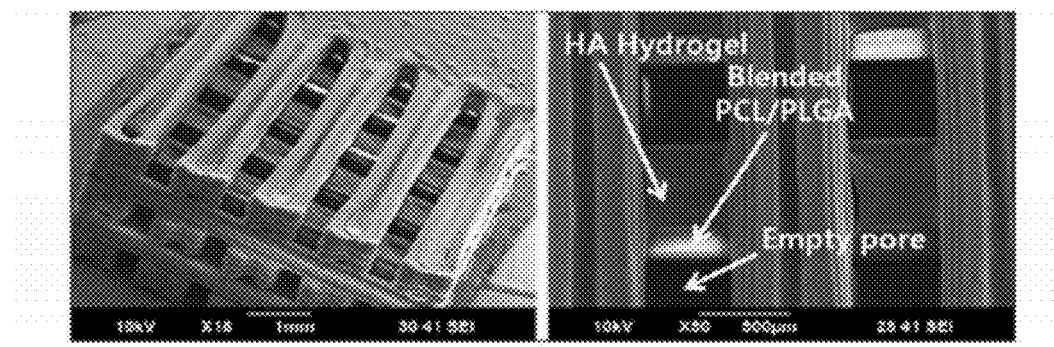
FIG. 1 is an enlarged picture of a scaffold that is manufactured according to an exemplary embodiment of the present invention.

In the following detailed description, only certain exemplary embodiments of the present invention have been shown and described, simply by way of illustration. In the drawings, a size of each element are randomly represented for better understanding and ease of description, and the present invention is not limited thereto.

FIG. 1 is an enlarged picture of a scaffold that is manufactured according to an exemplary embodiment of the present invention, and hereinafter, a scaffold according to the present exemplary embodiment will be described in detail with reference to FIG. 1.

A scaffold that is manufactured with a presently widely used biodegradable synthetic polymer does not provide a complete three-dimensional environment to a cell, and due to a relative hydrophobic property of a surface, when initially injecting a cell, thus there is a limitation that cell damage largely occurs and cell affinity is low.

A hydrogel is a material having a three-dimensional hydrophile polymer network structure that can contain a large amount of water and can absorb water of 20% to 95% of an entire weight, and such a natural polymer is a polymer that originates from a natural material, an animal, and a human body and has very excellent biocompatibility. Accordingly, a support that is manufactured with a hydrogel has a less inflammatory reaction after transplantation and has excellent biodegradability and thus is much used as a tissue engineering support. Further, there is a merit that under an aqueous solution environment, a cell, peptide, protein, or DNA can be protected and a product that supplies or secretes a nutrition source to a cell can be easily transferred and cell adhesion ligand can be easily received. However, when forming a support with only a hydrogel, use of the support can be limited only to regeneration of a soft tissue due to low mechanical strength, and in view of movement of a biodegradable material, the support can be easily decomposed by a body enzyme and thus until a tissue is regenerated, a problem that the support does not fully perform a function as a support may occur.

In order to overcome such a limitation, a scaffold according to the present exemplary embodiment includes both a biodegradable synthetic polymer and a hydrogel. Specifically, a plurality of biodegradable synthetic polymer-hydrogel layers including a biodegradable synthetic polymer and a hydrogel are formed and are formed in a lattice form by alternately stacking them.

In this case, the biodegradable synthetic polymer includes at least one of PLA, PGA, PCL, and PLGA. That is, a biodegradable synthetic polymer may be formed with one of the materials, or may be formed by mixing two or more materials.

Further, a natural polymer that can be applied as a hydrogel includes collagen, gelatin, chitosan, alginic acid, and hyaluronic acid.

By sealing a growth factor that can adjust growth and a function of a cell within a hydrogel, a scaffold may be formed, and in this case, as a growth factor, a transforming growth factor-β (TGF-β), bone morphogenetic protein (BMP), a VEGF, and an EGF can be used. As the growth factor exists within the hydrogel, tissue regeneration can be promoted. Further, by sealing a cell to regenerate within a hydrogel, a scaffold may be formed, and in this time, the growth factor may be together sealed.

In this way, by fusing a hydrogel to a biodegradable synthetic polymer, a scaffold can be formed, and thus a cell deposition ability and a propagation ability of the deposited cell can be improved, and a mechanical strength problem can be also solved.

FIG. 2 is a diagram illustrating a manufacturing system for manufacturing a scaffold according to an exemplary embodiment of the present invention, FIG. 3 is a flowchart illustrating a process of manufacturing a scaffold using such a manufacturing system, and FIGS. 4A to 4E are perspective views sequentially illustrating a process of manufacturing a scaffold according to an exemplary embodiment of the present invention, and hereinafter, a scaffold and a method of manufacturing the same according to an exemplary embodiment of the present invention will be described in detail with reference to the drawings.

As shown in FIG. 2, a scaffold manufacturing system forms a scaffold 200 of a three-dimensional shape using a multi-head deposition system 100.

The multi-head deposition system 100 has a stacking head 150 for ejecting a scaffold material of a predetermined thickness. The stacking head 150 includes a syringe 151 that injects and stores a material, a nozzle 153 that ejects a material that is injected into the syringe 151, and a heater 155 that appropriately sustains a temperature of a material, and in the present exemplary embodiment, a biodegradable synthetic polymer and a hydrogel are each injected into the syringes 151 of two stacking heads 150 and are ejected through each nozzle 153, whereby the scaffold 200 is formed.

In order to move the stacking head 150 in a z-axis direction of a vertical direction as well as a plane coordinate that is formed with an x-axis and an y-axis, the multi-head deposition system 100 includes an x-axis displacement moving unit 120 for moving the stacking head 150 in an x-axis direction, an y-axis displacement moving unit 130 for moving the stacking head 150 in an y-axis direction, and a z-axis displacement moving unit 140 for vertically moving the stacking head 150 in an z-axis direction. That is, the multi-head deposition system 100 can manufacture the scaffold 200 of a complicated three-dimensional shape to form in a shape by stacking a scaffold material on a work table 110 with a matrix method.

A shape of the scaffold 200 to manufacture is input to an integrated controller 10 through a data model 20. In this case, it is preferable that each coordinate value of the scaffold 200 of a three-dimensional shape is set to input the data model 20 of the scaffold 200 as three-dimensional CAD data.

The integrated controller 10 controls operation of the multi-head deposition system 100 according to a three-dimensional shape data model of the scaffold 200. Thereby, the multi-head deposition system 100 alternately ejects a scaffold material, i.e., a biodegradable synthetic polymer and a hydrogel while moving to a coordinate value to set the stacking head 150 according to three-dimensional shape data of the scaffold 200 that is transferred from the integrated controller 10.

A temperature controller 30 is connected to the stacking head 150 of the multi-head deposition system 100 to control a temperature of the syringe 151 of the stacking head 150. Specifically, the temperature controller 30 is connected to the heater 155 that is attached to the stacking head 150 to control the heater 155 and thus heats or sustains a biodegradable synthetic polymer and a hydrogel within the syringe 151 of the stacking head 150 to a preset temperature, whereby a scaffold material of the biodegradable synthetic polymer and the hydrogel can be changed or sustained in an appropriate state to eject and ejected to a preset thickness through the syringe 151 the stacking head 150. The temperature controller 30 is connected together to the integrated controller 10 as well as the multi-head deposition system 100 and can operate to interlock with movement of the stacking head 150.

A pressure controller 40 is connected to the stacking head 150 of the multi-head deposition system 100 to control a pressure that is transferred to the stacking head 150. That is, the pressure controller 40 is a means for controlling a pressure that is transferred to a pressure transfer device of the stacking head 150 and makes different an ejecting speed of a biodegradable synthetic polymer and a hydrogel that are ejected through the nozzle 153 of the stacking head 150. The pressure controller 40 according to the present exemplary embodiment transfers a pressure to the pressure transfer device of the stacking head 150 by a pneumatic method. For this purpose, the three-dimensional scaffold manufacturing system has a pneumatic device 50 that applies a direct pressure to the pressure transfer device of the stacking head 150, and the pneumatic device 50 is operated by the pressure controller 40. In this case, the pneumatic device 50 is independently connected to each shaft of the multi-head deposition system 100 and can variously adjust a pneumatic pressure for each shaft.

In this way, the scaffold manufacturing system using the multi-head deposition system 100 is a system having 4 shafts that can independently control a position, a temperature, and a pressure unlike a general single axis system, and can adjust a shape of the scaffold and a size of a pore using the manufacturing system.

Referring to FIG. 3, a method of manufacturing a scaffold according to the present exemplary embodiment includes step of injecting a biodegradable synthetic polymer and a hydrogel into syringes, respectively (S10), first ejecting step of ejecting a biodegradable synthetic polymer at a predetermined gap (S20), second ejecting step of ejecting a hydrogel between biodegradable synthetic polymer lines (S30), and step of alternately stacking biodegradable synthetic polymer-hydrogel layers (S40) and further includes step of controlling a temperature of a biodegradable synthetic polymer and a hydrogel that are injected into a syringe through a temperature controller.

A method of manufacturing such a scaffold will be described in detail with reference to FIGS. 4A to 4E.

First, in order to form the scaffold 200, data are transferred from the data model 20 to the integrated controller 10. The integrated controller 10 controls the temperature controller 30, the pressure controller 40, and the displacement moving units 120, 130, and 140 to each axis direction based on the transferred data.

After injecting a biodegradable synthetic polymer and a hydrogel into the syringes 151 of two stacking heads 150, respectively, a temperature of the syringe 151 is adjusted to sustain a state appropriate for injecting the biodegradable synthetic polymer and the hydrogel through the temperature controller 30 and the heater 155. In this case, as described above, one or two or more of PLA, PGA, PCL, and PLGA as a biodegradable synthetic polymer may be mixed and used, and one of collagen, gelatin, chitosan, alginic acid, and hyaluronic acid may be used as a hydrogel. For example, a biodegradable synthetic polymer may be melted and used in a state having viscosity by maintaining a material that is obtained by mixing PLGA and PCL in which a ratio of PLA and PGA is 85:15 at 90° at 120° through the temperature controller 30 and the heater 155, and a hydrogel may sustain and be used in appropriate viscosity by well stirring to be a gel state by mixing hyaluronic acid of a powder form with distilled water. In this case, because a hydrogel may be changed a material property thereof by a heat, a heat is not applied.

Thereafter, the stacking head receives the control of the displacement moving units 120, 130, and 140 and the pressure controller 40, and the scaffold 200 is formed by alternately ejecting a biodegradable synthetic polymer and a hydrogel on the work table 110 through the ejecting nozzle 153 of the stacking head 150. In the present exemplary embodiment, when ejecting a biodegradable synthetic polymer and a hydrogel, a pneumatic pressure is used, and the used pneumatic pressure is about 650 kPa.

Referring to FIGS. 4A and 4B, at first ejecting step S20, a biodegradable synthetic polymer is ejected over several lines at a predetermined gap. Thereby, a plurality of biodegradable synthetic polymer lines 210 are formed, and in order to eject a hydrogel between the biodegradable synthetic polymer lines 210, biodegradable polymers are stacked several times to have an appropriate height, as shown in FIG. 4B. In the present exemplary embodiment, a height of a layer of the biodegradable synthetic polymer line 210 is about 100 um, and a height of 300 um to 400 um is obtained by stacking the layer 3 to 4 times.

FIG. 4C illustrates second ejecting step S30 of ejecting a hydrogel, and at second ejecting step S30, by forming a biodegradable synthetic polymer line 210 at a predetermined gap, a hydrogel is ejected into a pore that is formed therebetween, and thus a plurality of hydrogel lines 220 are formed, and by controlling the ejecting nozzle 153 that ejects a hydrogel to position at the center of a pore, a hydrogel can be ejected at an accurate position. In this case, the reason why a hydrogel is ejected to every other pore is that a pore that can give and receive oxygen and a nutritive substance to and from the scaffold 200 is necessary and this is a method of securing the pore. In this way, a biodegradable synthetic polymer-hydrogel layer 240 of one layer is formed through first ejecting step S20 and second ejecting step S30. That is, the biodegradable synthetic polymer-hydrogel layer 240 is formed by disposing a biodegradable synthetic polymer-hydrogel unit 230 including a biodegradable synthetic polymer line 210 and a hydrogel line 220 at a predetermined gap and forming a pore between the biodegradable synthetic polymer-hydrogel units 230.

Figure 4E:
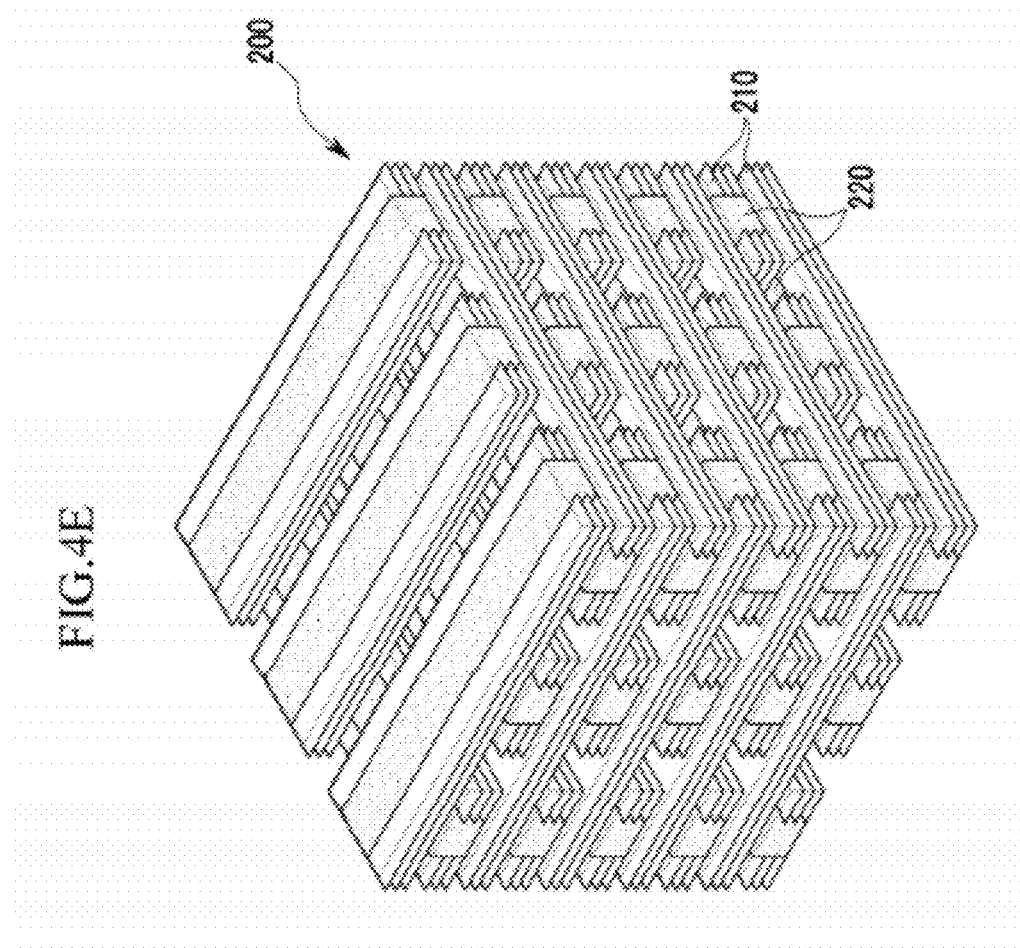

Stacking step S40 is step of stacking biodegradable synthetic polymer-hydrogel layers 240 in plural by repeating the first ejecting step S20 and the second ejecting step S30, and referring to FIG. 4D, after one layer is stacked, a next layer is stacked by entirely rotation the biodegradable synthetic polymer-hydrogel layers 240 by 90° and thus the scaffold 200 forms a lattice pattern. By repeatedly performing stacking step S40 until the biodegradable synthetic polymer-hydrogel layers 240 has a desired height, the scaffold 200 of a lattice pattern can be manufactured, as shown in FIG. 4E. For example, in order to obtain a scaffold of a height 2 mm, the biodegradable synthetic polymer-hydrogel layer 240 of a height 300 um to 400 um may be stacked 5 to 6 times.

In order to verify an effect of a scaffold according to the present exemplary embodiment, the following experiment was performed. For this experiment, PCL and PLGA are used as a biodegradable synthetic polymer and a case of using hyaluronic acid and a case of using gelatin as a hydrogel are divided, and a scaffold was manufactured according to the method of manipulating a scaffold. Further, for an experiment, MC3T3-E1 cell, which is a pre-osteoblast was used, and $10^5$ cells per scaffold was transplanted. In order to evaluate cell propagation, cell counting kit-8 was used, and a propagation evaluation was performed until 7 days.

Figure 5:
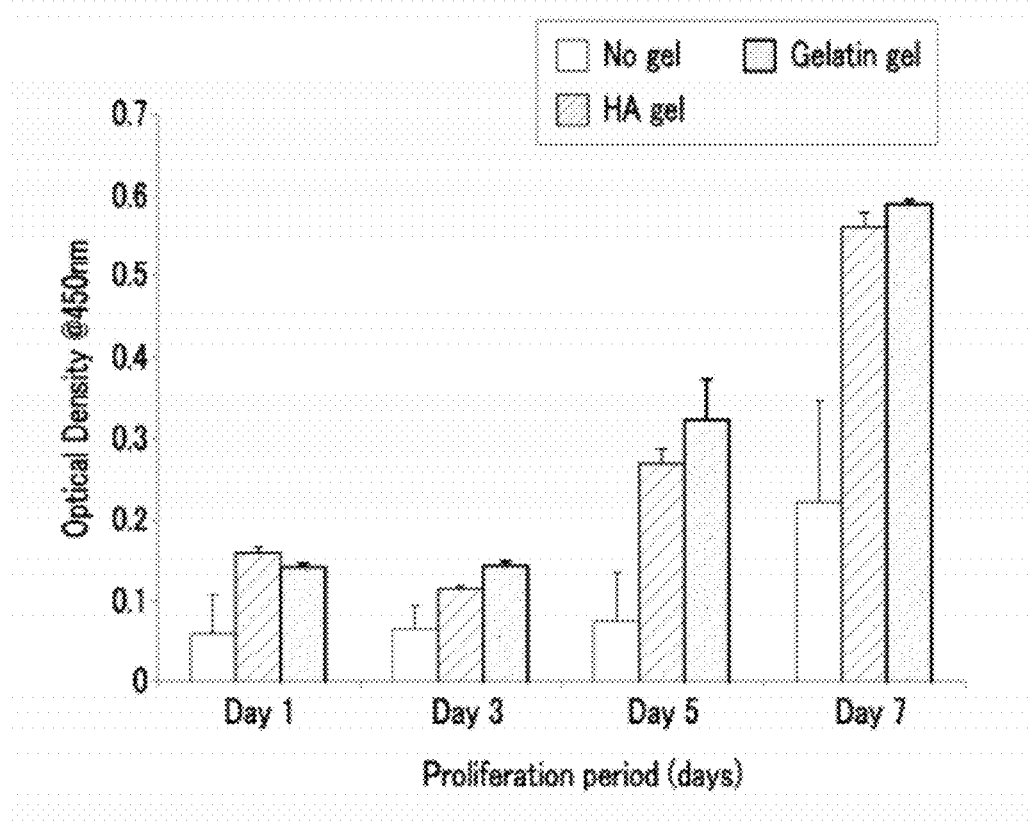
FIG. 5 is a graph illustrating a proliferation result of a cell in a scaffold that is manufactured according to an exemplary embodiment of the present invention.

FIG. 5 is a graph illustrating a cell proliferation result according to an experiment and illustrates that a cell deposition ability of scaffolds having a hydrogel and a propagation ability of deposited cells are is more excellent than those of a scaffold that does not include a hydrogel.

Thereby, according to the present exemplary embodiment, it can be determined that a scaffold including a biodegradable synthetic polymer and a hydrogel has excellent effect on cell propagation, and mechanical strength can be also improved, as described above. Further, by sealing together a cell and a growth factor that can help regeneration of a tissue within a scaffold, a tissue regeneration effect can be maximized.

As described above, an exemplary embodiment of the present invention is described, but the present invention is not limited to the foregoing exemplary embodiment. A pattern of a biodegradable synthetic polymer portion or an ejecting position of a hydrogel can be freely adjusted, and a scaffold of forms other than a lattice pattern may be manufactured using a multi-head deposition system.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of symbols>

| | |
|---|---|
| 10: integrated controller | 20: data model |
| 30: temperature controller | 40: pressure controller |
| 50: pneumatic device | 100: multi-head deposition system |
| 110: work table | 120: X-axis displacement moving unit |
| 130: Y-axis displacement moving unit | |
| 140: Z-axis displacement moving unit | |
| 150: stacking head | 151: syringe |
| 153: ejecting nozzle | 155: heater |
| 200: scaffold | |
| 210: biodegradable synthetic polymer line | |
| 220: hydrogel line | |
| 230: biodegradable synthetic polymer-hydrogel unit | |
| 240: biodegradable synthetic polymer-hydrogel layer | |

What is claimed is:

1. A scaffold that is formed in a lattice form by alternately stacking a plurality of biodegradable synthetic polymer-hydrogel layers wherein after one biodegradable synthetic polymer-hydrogel layer is stacked, the next biodegradable synthetic polymer-hydrogel layer is stacked by rotating the next biodegradable synthetic polymer-hydrogel layer by 90 degrees to form a lattice pattern,
    wherein each of the biodegradable synthetic polymer-hydrogel layers is formed by disposing a plurality of biodegradable synthetic polymer-hydrogel units spaced apart from each other at a pre-determined gap, each of the plurality of biodegradable synthetic polymer-hydrogel units comprises a biodegradable synthetic polymer and a hydrogel,
    wherein each of the plurality of biodegradable synthetic polymer-hydrogel units is formed by interposing a single hydrogel line between a pair of a plurality of biodegradable synthetic polymer lines stacked upon each other and fusing the single hydrogel line and the pair of the stacked plurality of biodegradable synthetic polymer lines.

2. The scaffold of claim 1, wherein the biodegradable synthetic polymer comprises at least one of poly-lactic acid (PLA), poly-glycolic acid (PGA), polycaprolactone, and poly-lactic-co-glycolic acid (PLGA).

3. The scaffold of claim 1, wherein the hydrogel is water-soluble.

4. The scaffold of claim 3, wherein the hydrogel is one of collagen, gelatin, chitosan, alginic acid, and hyaluronic acid.

5. The scaffold of claim 1, wherein a growth factor is sealed within the hydrogel.

6. The scaffold of claim 5, wherein the growth factor existing within the hydrogel is one of a transforming growth factor-β (TGF-β), bone morphogenetic protein (BMP), a vein endothelial cell growth factor (VEGF) and an epithelial cell growth factor (EGF).

7. The scaffold of claim 1, wherein a cell that is regenerated is sealed within the hydrogel.

* * * * *